United States Statutory Invention Registration [19]

[11] Reg. Number: H574

Merkel et al. [43] Published: Feb. 7, 1989

[54] SUBJECT OPERATED PUPILOMETER

[75] Inventors: Harold S. Merkel; David P. Ramer, both of Beavercreek, Ohio

[73] Assignee: The United States of America as represented by the Secretary of the Air Force, Washington, D.C.

[21] Appl. No.: 90,481

[22] Filed: Aug. 28, 1987

[51] Int. Cl.[4] ..... A61B 3/02; A61B 3/14

[52] U.S. Cl. ..... 351/223; 351/206; 351/224

[58] Field of Search ..... 351/205, 206, 221, 223, 351/224

[56] References Cited

U.S. PATENT DOCUMENTS

| | | | |
|---|---|---|---|
| 3,533,683 | 10/1970 | Stark et al. | 351/1 |
| 3,787,112 | 1/1974 | Lyons | 351/223 |
| 3,797,921 | 3/1974 | Kilmer et al. | 351/206 |
| 4,423,931 | 1/1984 | Shapiro | 351/206 |
| 4,586,796 | 5/1986 | Molteno | 351/206 |

*Primary Examiner*—Stephen C. Buczinski
*Assistant Examiner*—Linda J. Wallace
*Attorney, Agent, or Firm*—Bobby D. Scearce; Donald J. Singer

[57] ABSTRACT

An instrument for the self-examination of the eye of a subject is described which comprises a housing including a controllable light source for selectively illuminating the eye, an optical system for projecting along an optical axis an image of the eye so illuminated, photographic film for recording the image, the optical system being sized to provide a predetermined magnification of the image on the film, a transparent grid plate disposed along the optical axis between the light source and film for superimposing a set of calibrated lines onto the image of the eye, and a controllable shutter in the optical system for selectively exposing the film to the superposition of the images of the eye and of the calibrated lines. A flexible light shield surrounds the light source for resiliently contacting the contour of the face of the subject whereby extraneous light is excluded.

4 Claims, 2 Drawing Sheets

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

SUBJECT OPERATED PUPILOMETER

RIGHTS OF THE GOVERNMENT

The invention described herein may be manufactured and used by or for the Government of the United States for all governmental purposes without the payment of any royalty.

BACKGROUND OF THE INVENTION

The present invention relates generally to clinical instruments for the examination of eyes, and more particularly to a portable instrument for self-examination of the pupil of the eye.

Pupilometer instruments known in the art prior to the invention generally comprise large, substantially stationary devices which have significant power requirements and which need a separate operator to focus and align optics of the devices, to make measurements and to interpret results.

The invention described herein comprises a compact, portable subject operated instrument for rapid and accurate measurements of the eye in substantially any environment, and has particular field utility as a pupilometer in the self-administered examination of pupil dilation. The invention includes a flashlamp and power source for illuminating the eye a lens system for projecting an image of the eye onto photographic film, and a calibrated grid imaged onto the film simultaneously with the image of the eye. A padded forehead light shield excludes extraneous light during a measurement. The invention combines a light emitting diode system for accurate alignment of the eye with a telecentric lens system and calibrated photographic image in a small portable pupilometer having certain advantages over pupilometer instruments previously known in the art. For example, the invention provides eye image magnification which does not change with position relative to the instrument and has a very large depth of focus which compensates for variation in distance to various subjects' eyes corresponding to various facial contours, which ensures consistent resolution in the instrument from subject to subject and eliminates any need for a separate operator for the instrument.

It is therefore a principal object of the invention to provide an improved eye examination instrument.

It is another object of the invention to provide an instrument for self-administered examination of the pupil of an eye.

It is a further object of the invention to provide a subject operated pupilometer for self-examination of pupil dilation.

It is yet a further object of the invention to provide a portable subject operated pupilometer.

These and other objects of the invention will become apparent as the detailed description of representative embodiments proceeds.

SUMMARY OF THE INVENTION

In accordance with the foregoing principles and objects of the invention, an instrument for the self-examination of the eye of a subject is described which comprises a housing including a controllable light source for selectively illuminating the eye, an optical system for projecting along an optical axis an image of the eye so illuminated, photographic film for recording the image, the optical system being sized to provide a predetermined magnification of the image on the film, a transparent grid plate disposed along the optical axis between the light source and film for superimposing a set of calibrated lines onto the image of the eye, and a controllable shutter in the optical system for selectively exposing the film to the superposition of the images of the eye and of the calibrated lines. A flexible light shield surrounds the light source for resiliently contacting the contour of the face of the subject whereby extraneous light is excluded.

DESCRIPTION OF THE DRAWINGS

The invention will be clearly understood from the following detailed description of representative embodiments thereof read in conjunction with the accompanying drawings wherein.

DETAILED DESCRIPTION

Figure 1:
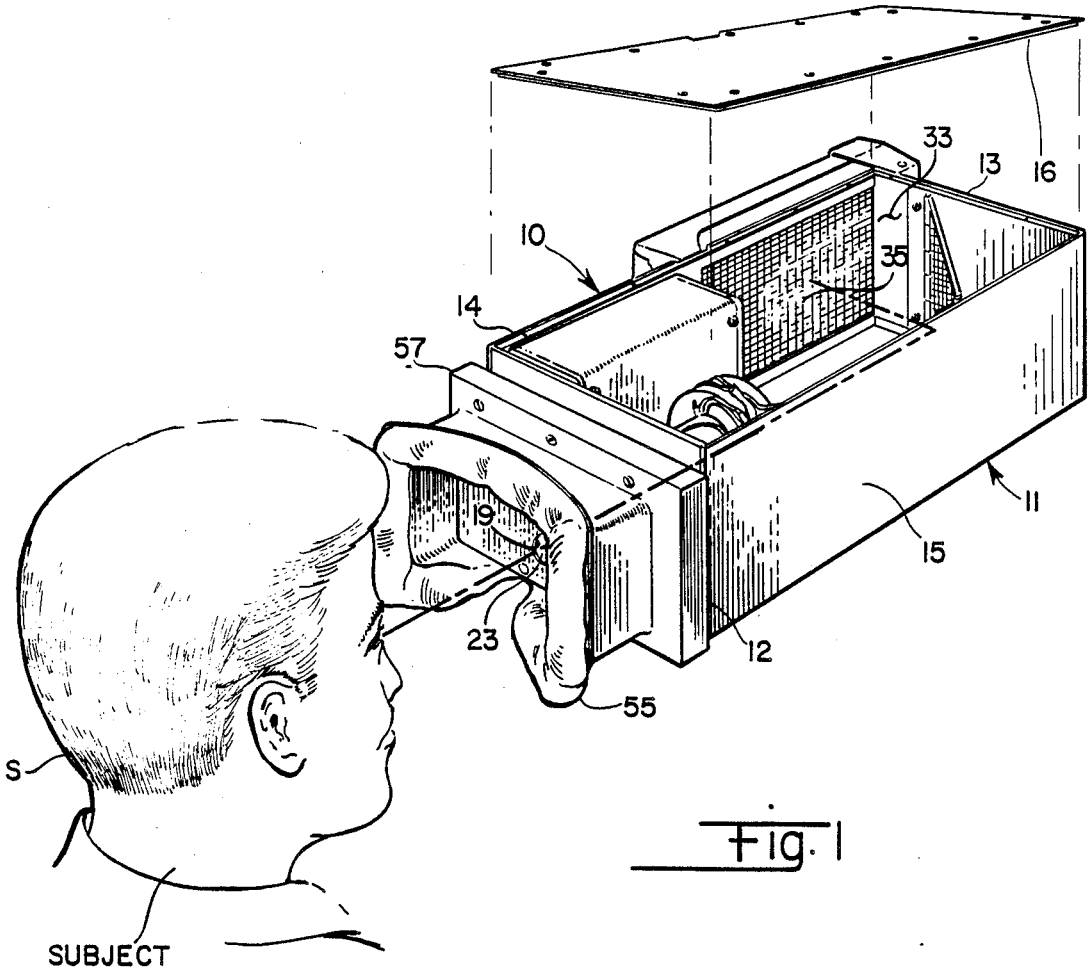
FIG. 1 is a perspective view of a representative pupilometer of the invention as viewed by a subject, wherein one wall of the pupilometer is shown broken away to reveal the internal components.
Figure 2A:
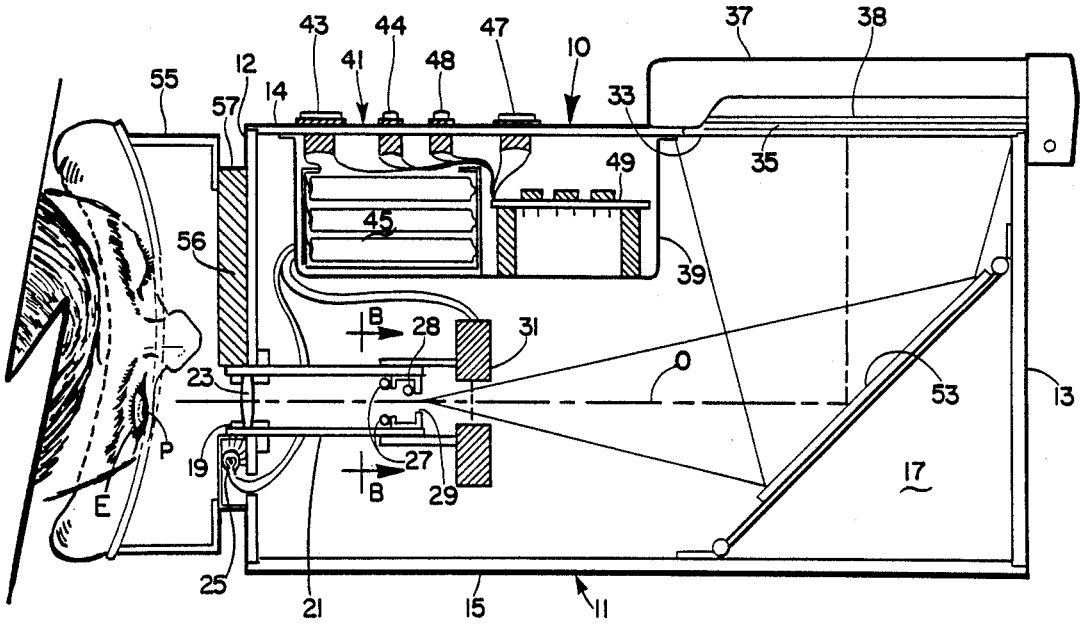
FIG. 2*a* is a schematic plan view of the optical, electronic and structural components of the invention.

Referring now to the drawings, shown in FIG. 1 is a perspective view of a representative pupilometer 10 of the invention as viewed by subject S. FIG. 2*a* is a schematic plan view of the optical and electronic components of pupilometer 10. pupilometer 10 comprises a substantially light-tight housing 11 having front and back walls 12,13, side walls 14,15, and top and bottom walls 16,17. Top wall 16 is shown broken away in FIG. 1 to reveal internal components of pupilometer 10. Housinq 11 may comprise any suitable material as would occur to one skilled in the appropriate art; in a unit built in demonstration of the invention housing 11 comprised 3/16 inch aluminum plate and had dimensions of about $11\times4.5\times5.5$ inches. Opening 19 in front wall 12 receives and supports sighting tube 21 disposed along optical axis O along which subject S sights in using pupilometer 10. Lens 23 (in the demonstration unit an achromatic lens, focal length 50 mm, diameter 23 mm) mounted within opening 19 of wall 12 functions as an eyepiece in the optics of pupilometer 10. Flashlamp 25 (e.g., xenon type) is mounted near opening 19 for selectively illuminating eye E in the operation of pupilometer 10.

Figure 2B:
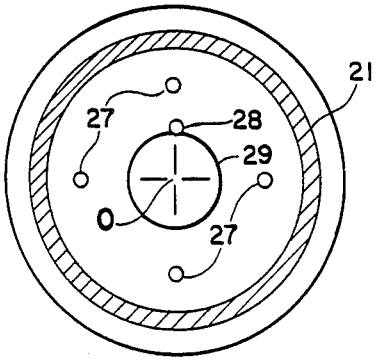
FIG. 2*b* is a view along line B—B of FIG. 2*a;*

Referring now additionally to FIG. 2*b*, which is a view along line B—B of FIG. 2*a* a plurality of alignment light emitting diodes 27 (LEDs) are mounted within sighting tube 21 around axis O. In the demonstration unit, four LEDs 27 were mounted in quadrature around axis O, and a fifth LED 28 was mounted near axis O centrally of LEDs 27. An aperture 29 is disposed along axis O and spaced from lens 23 a distance equal to the focal length of lens 23. In the demonstration unit, aperture 29 was sized at 1 mm and spaced 50 mm from lens 23. A controllable shutter 31 (in the demonstration unit an electronic shutter. Ilex electronic w/flash synchronization #04 IES 001 ) is disposed adjacent aperture 29 at one end of sighting tube 21 as suggested in FIG. 2a.

Figure 3:
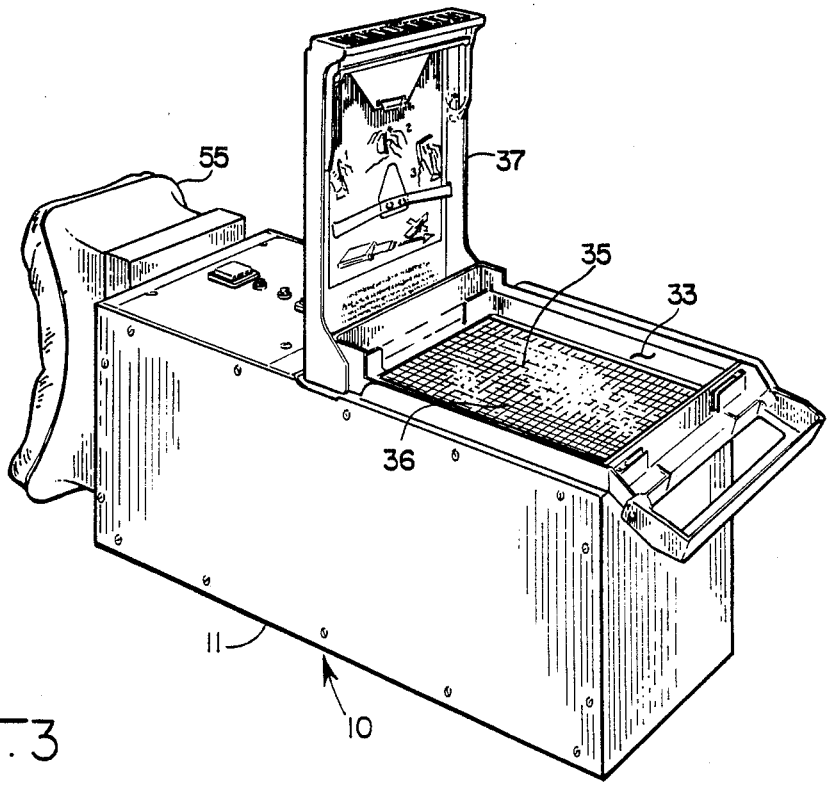
FIG. 3 is a perspective view of the electronic control panel, grid and film holder of the FIG. 1 embodiment.

Referring now collectively to FIGS. 1, 2a and 3, a transparent grid plate 35 having thereon a plurality of calibrated grid lines 36 may be mounted at a suitable location along axis O such as in opening 33. In the demonstration unit, grid plate 35 was 3/32 inch plexiglass with enscribed 5 mm square grid pattern and is discussed more fully below in relation to FIG. 4. The purpose of grid plate 35 is to superimpose a set of calibrated lines onto the image of eye E projected along axis O. Accordingly, as would occur to the skilled artisan, grid plate 35 may in alternative embodiments be disposed at other locations along axis O at which the magnification of the optical system is known, e.g.. as a reticle (eyepiece) at lens 23, or superimposed using a beam-splitter from a separate optical axis. Film holder 37 (e.g., polaroid model #405) containing photographic plate or film 38 is mounted to housing 11 such as shown for photographically recording an image of eye E.

Power source and electronic controls for pupilometer 10 may, as in the demonstration unit, take the form of an electronic control module 39 mounted within housing 11 and presenting at wall surface 14 a control panel 41 including various switches and displays for control of pupilometer 10, such as power switch 43 and power on/off indicator light (LED) 44 operatively connected to power source 45, shutter control switch 47, and timing (LED) light 48 operatively connected to timer 49, flashlamp 25 and shutter 31.

Grid plate 35 and film holder 37 may be mounted at any suitable wall of housing 11, the arrangement shown in the drawings having these components mounted in side wall 14 being only exemplary. The mounting shown may best be accommodated using optical folding mirror 53 disposed along axis O at a suitable location to fold the projected image of eye E. Use of folding mirror 53 along axis O provides an advantage of minimizing overall size of housing 11 for a given optical path length from lens 23 to film 38. In the demonstration unit, housing 11 was sized and mirror 53 was placed such that the optical distance from aperture 29 to film 38 was five focal lengths of lens 23. It is understood that sizing of housing 11 and lens 23 are not critical to the invention so long as system magnification is calculable for calibration purposes.

Mask 55 mounted on front wall 12 shields extraneous light from the eye E during a measurement. In the demonstration unit, mask 55 was designed to an anthropomorphic model for fit to substantially all subjects while forming a light seal at the face contour of subject S. It is noted that the embodiment of the invention shown in the figures has a single eyepiece lens 23 and sighting tube 21 for examination of a single eye E (viz., the right eye as shown in FIG. 1). In order to best accommodate examination of the other eye, mask 55 may be mounted to housing 11 through a (aluminum) plate 56 and spring loaded pivot mechanism 57, whereby a selected eye may be examined by pulling mask 55 outwardly from housing 11 and rotating it into in the desired orientation. Control panel 41 is therefore best accessible to one hand for examination of the right eye and to the other hand for examination of the left eye.

The invention as configured in the representative embodiment described above and depicted in the drawings is intended for use in the measurement of pupil P of a subject substantially as follows. With the power on, subject S holds pupilometer 10 in front of eye E with mask 55 against the face to exclude extraneous light. The alignment LEDs 27 are viewed as eye E adjusts to the dark within mask 55. Pressing shutter control switch 47 starts an (optional) 60 second delay to ensure accommodation of eye E to the dark. After 60 seconds, LED 28 appears centrally of LEDs 27. The optics of pupilometer 10 are aligned such that when subject S sights along axis O so that LED 28 appears centered vertically and horizontally of LEDs 27, eye E is aligned properly for imaging onto film 38. Pressing shutter control switch 47 again activates shutter 31 and flashlamp 25. The desired image of eye E is thereby projected along axis O to film 38.

Since aperture 29 in the demonstration unit was located one focal length from the principal plane of lens 23, only parallel rays incident on lens 23 passed along axis O. Additionally, the distance from aperture 29 to film 38 was selected at 5× the focal length which, together with the one focal length lens-aperture spacing, provided an optical system telecentric in object space with a transverse magnification of five.

Once film 38 is exposed, a print may be removed from film holder 37 and developed. The electronics of pupilometer 10 may include a timer set to an appropriate development time for film 38.

Figure 4:
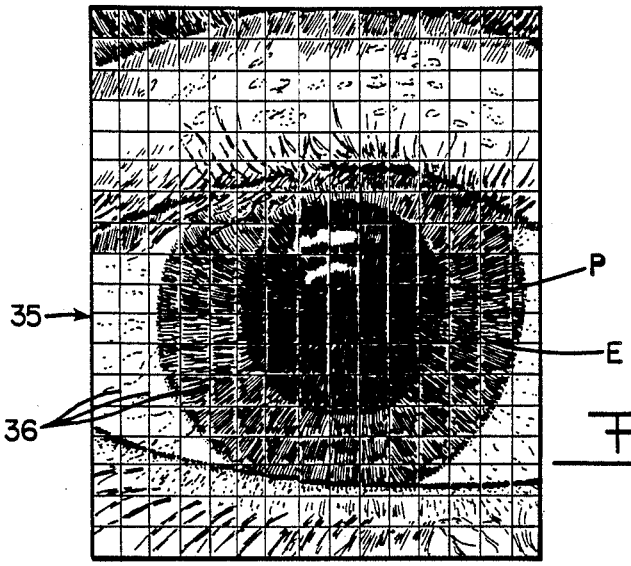
FIG. 4 is a schematic of a representative photographic image of an eye and superimposed grid obtained using the invention.

Referring now to FIG. 4, shown therein is a schematic of a representative photographic image of eye E and superimposed grid lines 36 obtained using pupilometer 10 as just described. Grid lines 36 are precalibrated according to the dimensions and spacings of the optical components. In the demonstration unit, the spacing between adjacent grid lines 36 on grid plate 35 corresponded to one millimeter on the image of eye E. Examination of the number of grid units spanning the image of pupil P on the photographic image obtained as above exemplified by FIG. 4 yields pupil size.

The demonstration unit included other noteworthy optional features including a safety feature preventing operation of shutter 31 and flashlamp 25 if shutter control switch 47 is pressed at other than the proper time during a measurement; i.e., following proper alignment of eye E and pressing switch 47, inadvertently pressing switch 47 a second time before 60 seconds elapses has no effect and flashlamp 25 will not activate until the proper time elapses.

The invention therefore provides a novel portable subject operated pupilometer. It is understood that modifications to the invention may be made as might occur to one with skill in the field of the invention within the scope of the claims. All embodiments contemplated hereunder which accomplish the objects of the invention have therefore not been shown in complete detail. Other embodiments may be developed without departing from the spirit of the invention or from the scope of the claims.

We claim:

1. An instrument for the self-administered measurement of the pupil of the eye of a subject, comprising:

(a) a controllable light source for selectively illuminating said eye of said subject;

(b) optical means for projecting along an optical axis an image of said eye so illuminated;

(c) photographic film disposed along said optical axis for recording said image of said eye, said film disposed a preselected distance from said optical means providing a predetermined magnification of said image of said eye on said film;

(d) a substantially transparent plate having thereon a set of calibrated lines disposed along said optical axis adjacent said film for superimposing a set of calibrated lines onto said image of said eye;

(e) a controllable shutter disposed along said optical axis for slectively exposing said film to the superposition of said image of said eye and an image of said calibrated lines; and (f) a light shield surrounding said light source for resiliently contracting the face of said subject and excluding extraneous light from said optical means.

2. The instrument of claim 1 wherein said optical means comprises an eyepiece lens.

3. The instrument of claim 1 further comprising an aperture of preselected size disposed along said optical axis for selectively exposing said film to the superposition of said image of said eye and said image of said calibrated lines.

4. The instrument of claim 2 wherein said optical means includes a telecentric lens system providing said predetermined magnification independent of the spacing between said eye of said subject and said eyepiece lens.

* * * * *